United States Patent [19]

Schumann

[11] Patent Number: Plant 5,942

[45] Date of Patent: Apr. 14, 1987

[54] GERANIUM PLANT NAMED CHAMPAGNE

[75] Inventor: Ingeborg Schumann, Bad Ems, Fed. Rep. of Germany

[73] Assignee: Fischer Geraniums, Inc., Netherlands Antilles

[21] Appl. No.: 761,101

[22] Filed: Jul. 31, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Champagne having light rose flower color; single flower form; round flower type; early flowering response and excellent flower production; light leaf zonation; excellent temperature tolerance; good branching and medium growth habit.

1 Drawing Figure

The present invention comprises a new and distinct cultivar of geranium, botanically known as *Pelargonium zonale,* and hereinafter referred to by the cultivar name Champagne.

Champagne is a product of a planned breeding program which had the objective of creating new geranium cultivars having a light rose flower color, single flower form, good growing characteristics, fast rooting, good flowering response and resistance to rain.

Champagne was originated from a hybridization made by Ingeborg Schumann in a controlled breeding program in Hillscheid, Federal Republic of Germany in 1979. The female parent was a cross between Hönnefrühling and Bianca. The male parent of Champagne was Lachsball. Both parents are unpatented.

Champagne was discovered and selected as one flowering plant within the progeny of the stated cross by Ingeborg Schumann on July 24, 1980 in a controlled environment in Hillscheid, Federal Republic of Germany.

The first act of asexual reproduction of Champagne was accomplished when vegetative cuttings were taken from the initial selection in January of 1981 in a controlled environment in Hillscheid, Federal Republic of Germany by a technician working under formulations established and supervised by Ingeborg Schumann. Horticultural examination of selected units initiated in the spring of 1981 and continuing in 1982 and 1983 has demonstrated that the combination of characteristics as herein disclosed for Champagne are firmly fixed and are retained through successive generations of asexual reproduction.

Champagne has not been observed under all possible environmental conditions. The phenotype may vary significantly with variations in environment such as temperature, light intensity, and day length. The following observations, measurements and comparisons describe plants grown in Hillscheid, Federal Republic of Germany, under conditions which approximate those generally used in commercial practice.

The following traits have been repeatedly observed and are determined to be basic characteristics of Champagne, which in combination distinguish this geranium as a new and distinct cultivar.

1. Light rose flower color.
2. Single flower form.
3. Round flower type.
4. Good rooting and fast cultivation.

5. Light leaf zonation.
6. Good branching habit and medium growth habit, making Champagne ideal for bedding plant production.
7. Excellent temperature tolerance.
8. Early flowering response and excellent flower production.

Of the many commercial cultivars known to the present inventor, the most similar in comparison to Champagne is Hönnefrühling which has a light rose flower color and single flower form. Reference is made to the attached Chart A which compares certain characteristics of Champagne to those same characteristics of Hönnefrühling. In comparison to Hönnefrühling, Champagne has better rooting, a faster growing period, better temperature tolerance, and a lighter zonation.

The accompanying photographic drawing shows typical flower and foliage characteristics of Champagne, with colors being as true as possible with illustrations of this type.

In the following description color references are made to The Royal Horticultural Society Colour Chart. The color values were determined between 3:00 p.m. and 4:00 p.m. on May 15, 1985 under 25,000 Lux light intensity at Hillscheid, Federal Republic of Germany.

Classification:

*Botanical.*—A hybrid of the genus Pelargonium l'hert and species *Pelargonium zonale.*

*Commercial.*—Champagne.

INFLORESCENCE

A. Umbel:

*Average diameter.*—99 mm.

*Average depth.*—77 mm.

*Peduncle length.*—200 mm.

*Pedicel length.*—23 mm.

B. Corolla:

*Average diameter.*—48 mm.

*Form.*—Single, nearly round.

*Color (general tonality from a distance of three meters).*—Pink. Upper surface: mainly 55D, lighter at margin and darker at center.

C. Bud:

*Shape.*—Elongated; pointed.

*Color.*—White to salmon.

D. Reproductive organs:

Androecium.—7–8 anthers.

*Gynoecium.*—4–5 lobed stigma.

E. Spring flowering response period: In Hillscheid, Federal Republic of Germany, in 1983, 70% of plants opened with at least one flower 13 weeks after planting of unrooted cuttings.

F. Outdoor flower production: The total flower count in 1983 in Hillscheid, Federal Republic of Germany, was between 61 and 65 flowers per plant for the June through October observation period.

G. Durability: Shatter resistance good.

PLANT

A. Foliage:

*Form.*—Kidney shaped.

*Margin.*—Scalloped.

*Color.*—Top surface; Medium green, approximately 137B–C. Zonation: Light zonation.

*Tolerance of botrytis.*—Good.

B. General appearance and form:

*Internode length.*—32 mm.

*Branching pattern.*—3.3 branches per plant within a period of 13 week cultivation from unrooted cuttings.

*Height.*—310 mm.

CHART A

| CULTIVAR | ZONATION | ROOTING | GROWTH |
|---|---|---|---|
| Honnefruhling | Strong | Bad | Bad |
| Champagne | Light to medium | Good | Good |

| CULTIVAR | FLOWER RESPONSE | BRANCHING |
|---|---|---|
| Honnefruhling | 45–49 | 3.0 |
| Champagne | 61–65 | 3.3 |

I claim:

1. A new and distinct cultivar of geranium named Champagne, as described and illustrated, and particularly characterized by its light rose flower color; single flower form; round flower type; early flowering response and excellent flower production; light leaf zonation; excellent temperature tolerance; good branching and medium growth habit.

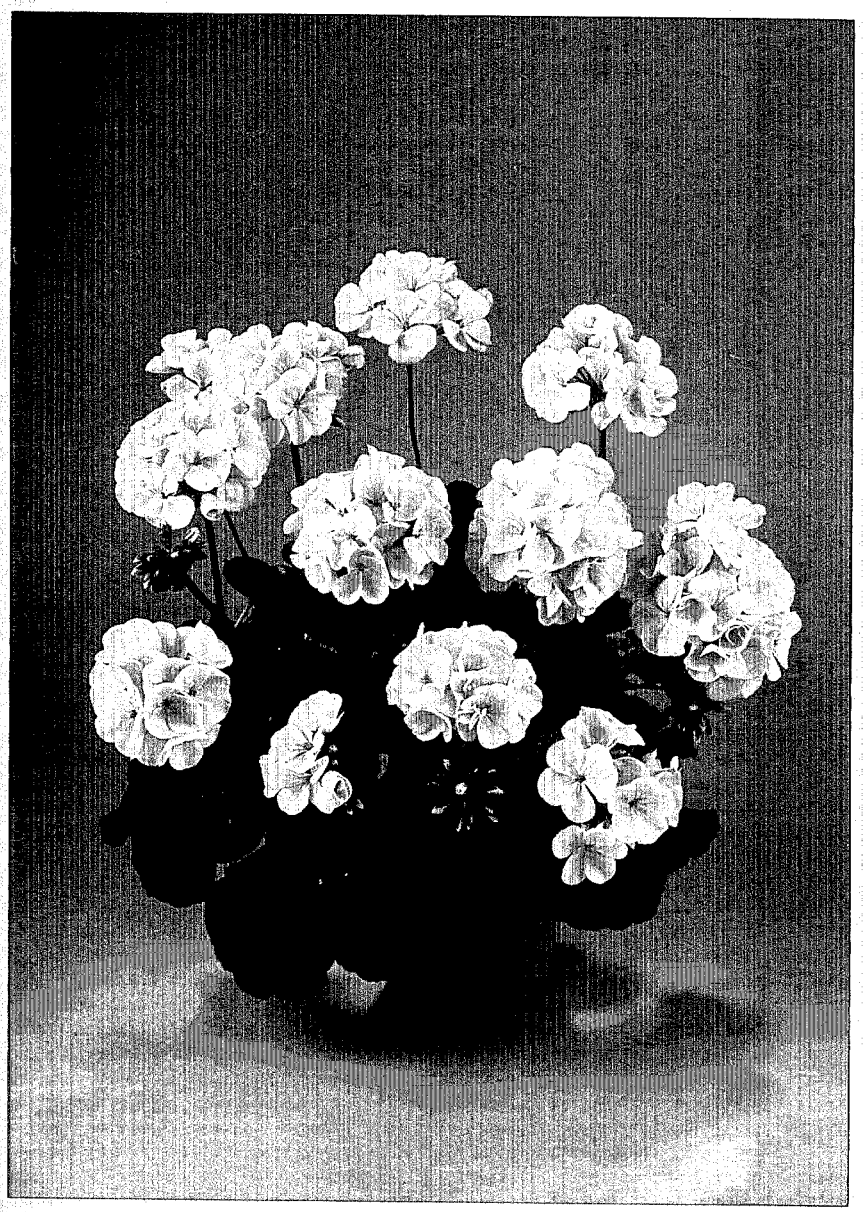

* * * * *